US006245111B1

(12) United States Patent
Shaffner (10) Patent No.: US 6,245,111 B1
(45) Date of Patent: Jun. 12, 2001

(54) METHOD AND APPARATUS FOR FIGHTING INFECTION AND MAINTAINING JOINT SPACING IN A PROSTHESIS IMPLANT AREA

(76) Inventor: Richard L. Shaffner, 1624 Manhasset Farm Rd., Dunwoody, GA (US) 30338

( * ) Notice: Subject to any disclaimer, the term of this patent is extended or adjusted under 35 U.S.C. 154(b) by 0 days.

(21) Appl. No.: 09/351,957

(22) Filed: Jul. 12, 1999

Related U.S. Application Data (63) Continuation-in-part of application No. 08/854,445, filed on May 12, 1997, now Pat. No. 5,980,573.

(51) Int. Cl.[7] ............................. A61F 2/32; A61F 2/40
(52) U.S. Cl. ............... 623/22.4; 623/22.15; 623/23.21; 623/23.44; 623/23.62; 606/99
(58) Field of Search .................. 623/22.4, 22.15, 623/23.21, 23.44, 23.62; 606/99

(56) References Cited

U.S. PATENT DOCUMENTS

| 3,938,198 | * | 2/1976 | Kahn et al. | 623/22.15 |
| 4,516,277 | * | 5/1985 | Butel | 623/23.18 |
| 4,851,007 | * | 7/1989 | Gray | 623/22.46 |
| 4,919,666 | * | 4/1990 | Buchhorn et al. | 623/16.11 |
| 4,919,679 | * | 4/1990 | Averill et al. | 623/22.12 |
| 5,123,927 | * | 6/1992 | Duncan et al. | 623/20.21 |
| 5,133,771 | * | 7/1992 | Duncan et al. | 623/23.2 |
| 5,286,763 | * | 2/1994 | Gerhart et al. | 514/772.4 |
| 5,370,698 | * | 12/1994 | Heimke et al. | 623/22.15 |
| 5,693,099 | * | 12/1997 | Harle | 23/22.15 |
| 5,888,208 | * | 3/1999 | Ro | 623/23.15 |
| 5,980,573 | * | 11/1999 | Shaffner | 623/22.4 |

* cited by examiner

Primary Examiner—Corrine McDermott
Assistant Examiner—Choon P. Koh
(74) Attorney, Agent, or Firm—Thomas, Kayden, Horstemeyer & Risley (57) ABSTRACT

The present invention relates to a prosthetic device for placement in an implant area of the body. The prosthetic device comprises an elongated stem portion, a neck portion, and a head portion. Each of the stem, neck, and head portions comprise a material impregnated with an antibiotic agent such that, when the prosthetic device is inserted into the implant area in place of a weight-bearing prosthesis, the antibiotic agent can leach out of the material to fight infection in the implant area. As an added benefit, the structure of the prosthetic device maintains adequate joint spacing in opposition to contraction of the muscles and tendons of the patient over a period of time so that a weight-bearing prosthesis can again be implanted into the implant area after the infection has been overcome.

10 Claims, 5 Drawing Sheets

METHOD AND APPARATUS FOR FIGHTING INFECTION AND MAINTAINING JOINT SPACING IN A PROSTHESIS IMPLANT AREA

CROSS-REFERENCE TO RELATED APPLICATION

This application is a continuation-in-part of U.S. patent application Ser. No. 08/854,445, filed May 12, 1997 U.S. Pat. No. 5,980,573.

FIELD OF THE INVENTION

The present invention generally relates to a method and apparatus for fighting infection and maintaining joint spacing in a prosthesis implant area of joint replacement patients. More particularly, the present invention relates to a temporary non-weight bearing prosthesis which includes a cementitious substance that is impregnated with an antibiotic agent which will leach out of the substance to fight infection in the implant area. The invention further relates to a method of forming and inserting the temporary non-weight bearing prosthesis into the implant area of the patient such that the joint spacing of the patient is maintained until the time at which a weight bearing prosthesis can be implanted.

BACKGROUND OF THE INVENTION

Bodily infection is a major concern for patients having implanted structures such as total knee or total hip replacements. In that any object implanted into the human body is foreign, regardless of the duration of time it has existed within the body, infection originating from even remote areas of the body can cause complications with the implanted object. For example, if the patient were to become infected from a rusted nail, the infection likely would spread to the tissue surrounding a joint implant.

Several different procedures have been developed in the past to prevent the formation and spread of infection in an implant area. One such procedure has been to administer large doses of antibiotics to the patient in hopes of eradicating the infection all together. Although this procedure is very simple and straightforward, it unfortunately rarely cures the patient of the infection by itself.

A more effective solution has been to remove the implant and replace it with some form of spacer containing an antibiotic agent. For example, in the case of total knee replacement patients, physicians often remove the femoral and tibial prostheses and the polyethylene "meniscus" positioned therebetween and replace them with a puck-shaped spacer made of bone cement impregnated with an antibiotic. Typically, the spacer is formed during the operation on a side table in the operating room so that the surgeon can first inspect the joint to determine what size spacer will be needed. After the appropriate size has been ascertained, the surgeon or an assistant simply mixes the constituent elements of the bone cement, typically a polymer and a monomer that will form polymethylmethacrylate, and adds an appropriate amount of antibiotic, typically in powder form. Once the bone cement begins to harden, it becomes malleable and may be shaped by hand to fit within the implant area of the patient where the primary prosthesis had once been. When the spacer has adequately hardened, it is then inserted into the implant area and the incision closed in the conventional manner.

Positioned in the implant area, the antibiotic slowly leaches out from the bone cement and into the surrounding tissue to prevent the formation and spread of the infection. While the infection is being fought, typically over a period of 4 to 6 weeks, the bone cement spacer maintains the amount of joint spacing that was present in the implant area prior to removal of the primary prosthesis. If some form of spacer were not placed in the implant area, this joint spacing would be substantially reduced due to the contraction of the muscles and tendons of the patient during the recuperation period.

Antibiotic-impregnated bone cement has also been utilized to prevent the formation and spread of infection in total hip replacement patients. In this scenario, the acetabular cup and the hip stem of the primary hip prosthesis are first removed. Next, the surgeon mixes the polymer, monomer, and the antibiotic agent and forms small beads of bone cement. These beads of bone cement are then positioned in a spaced relationship along a length of stainless steel suture wire. Once the bone cement has adequately hardened, the wire, together with the beads, is inserted into the femoral canal to destroy any infection present within the femur. After the infection has been overcome, the surgeon withdraws the beads of bone cement by simply pulling the suture wire out of the femoral canal, carefully counting the number of beads removed to ensure that no beads remain in the femur.

Unlike the knee spacer, the bead and suture wire device does not maintain the joint spacing of the implant area since the device does not occupy any of the acetabular cavity that the head and the acetabular cup of the primary hip prosthesis previously occupied. Since the joint will be immobilized and the patient often bedridden for a substantial period of time, contraction of the unused muscles and tendons can cause substantial joint spacing shrinkage. Although this shrinkage is not in itself harmful to the patient, it will shorten the patient's limb requiring the patient to either walk with a limp or use some form of orthotic device to compensate for the shortened limb. While it is sometimes possible for the physician to stretch the muscles and tendons of the patient to restore some of this lost spacing, it is unlikely that the patient will regain the full amount of joint spacing he or she had before the primary hip prosthesis was removed.

Accordingly, it can be seen that it would be desirable to provide a method and apparatus for fighting infection in an implant area of a patient which also maintains adequate joint spacing.

SUMMARY OF THE INVENTION

The present invention relates to a prosthetic device for placement in an implant area of the body. The prosthetic device comprises an elongated stem portion having a lower distal end and an upper proximal end, a neck portion having a lower distal end and an upper proximal end, the lower distal end of the neck portion being connected to the upper proximal end of the elongated stem portion, the neck portion extending upwardly from the elongated stem portion, and a head portion connected to the upper proximal end of the neck portion. Each of the stem, neck, and head portions comprise a material impregnated with an antibiotic agent such that, when the prosthetic device is inserted into the implant area in place of a weight-bearing prosthesis, the antibiotic agent can leach out of the material to fight infection in the implant area. As an added benefit, the structure of the prosthetic device maintains adequate joint spacing in opposition to contraction of the muscles and tendons of the patient over a period of time so that a weight-bearing prosthesis can again be implanted into the implant area after the infection has been overcome.

In addition, the invention relates to a method of preventing the spread of infection and maintaining joint spacing in an implant area of a joint replacement patient that comprises examining the implant area to determine the size and extent of the joint spacing, selecting a prosthetic device comprising antibiotic-impregnated material and sized to fit within the implant area such that, once inserted within the implant area, little or no space is left between the prosthetic device and the surrounding tissue of the implant area, the pre-formed temporary hip prosthesis having an elongated stem, a neck portion, and a head. The prosthetic device is then inserted into the implant area such that the antibiotic can leach out of the antibiotic-impregnated material to fight infection and to maintain adequate joint spacing in opposition to contraction of the muscles and tendons of the patient so that a weight-bearing prosthesis can be implanted into the implant area after the infection has been overcome.

The features and advantages of the present invention, will become apparent upon reading the following detailed description, when taken in conjunction with the accompanying drawings.

DESCRIPTION OF THE PREFERRED EMBODIMENTS

Figures 1, 2, 3:
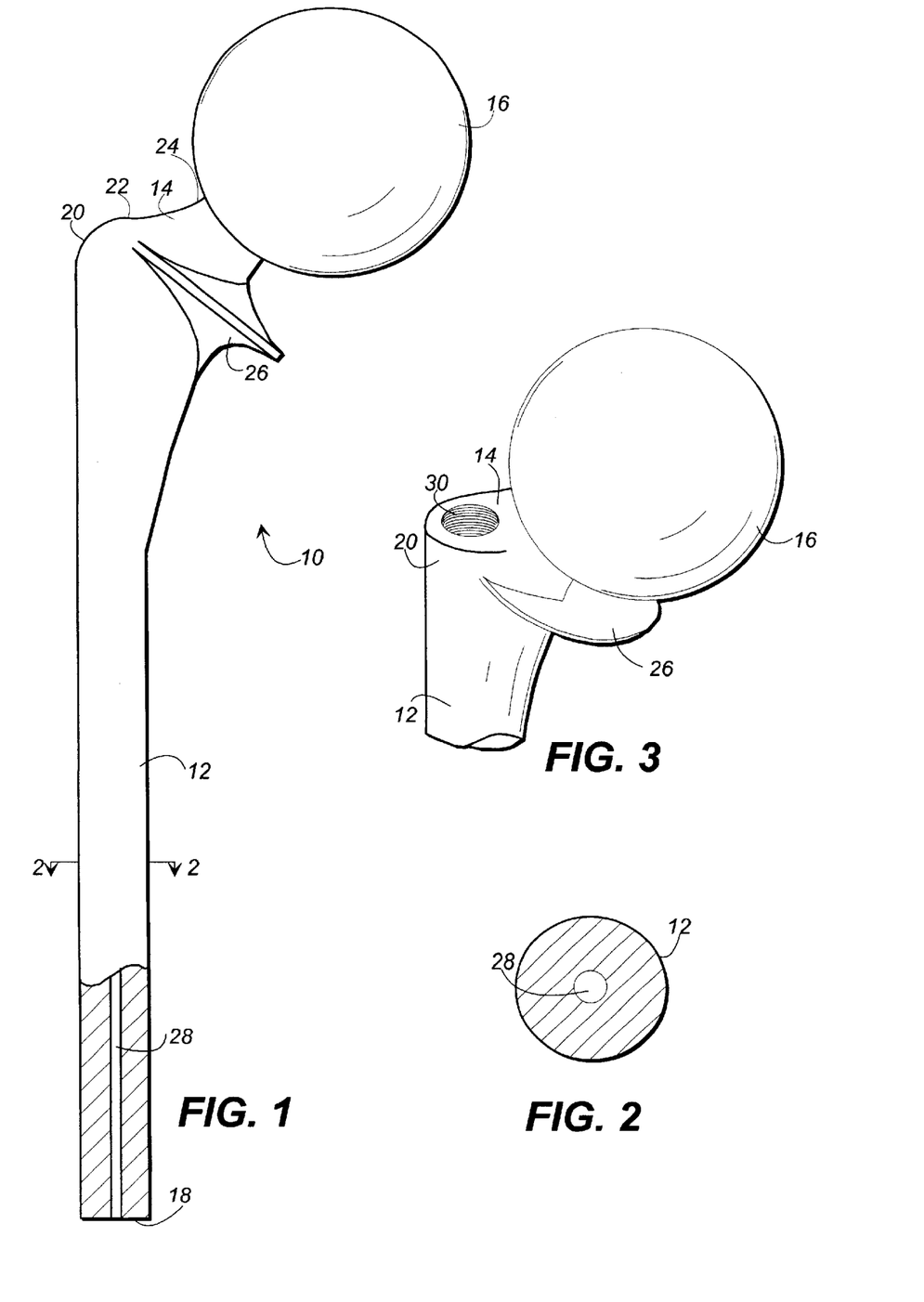
FIG. 1 is a side view, partially in section of a pre-formed temporary hip prosthesis.
FIG. 2 illustrates a cross-sectional view of the pre-formed temporary hip prosthesis shown in FIG. 1.
FIG. 3 is a perspective view of a threaded aperture of an alternative embodiment of the pre-formed temporary hip prosthesis.

Referring now in greater detail to the drawings in which like numerals indicate corresponding parts throughout the several views, FIG. 1 illustrates an embodiment of a pre-formed temporary hip prosthesis 10 to be inserted in place of a weight bearing hip prosthesis of a total hip stem replacement patient. As shown in the figure, the pre-formed temporary hip prosthesis 10 comprises an elongated stem portion 12, a neck portion 14, and a head portion 16. The elongated stem portion 12 typically is substantially cylindrical in shape and has a lower distal end 18 and an upper proximal end 20. Where the shape selected is cylindrical, the elongated stem portion 12 can be tapered along its length and usually will have a substantially circular cross-section as depicted in FIG. 2.

Similar to the elongated stem portion 12, the neck portion 14 has a lower distal end 22 and an upper proximal end 24.

As shown most clearly in FIG. 1, the neck portion 14 extends from the upper proximal end 20 of the elongated stem portion 12 at an angle to simulate the configuration of a human femur. The neck portion 14 can be formed substantially cylindrically as indicated in FIG. 1, or may take any other shape which would substantially simulate the function of a human femur.

The head portion 16 of the prosthesis 10 is formed on the upper proximal end 24 of the neck portion 14. Typically, the head portion 16 is substantially spherical, forming a bulbous head which simulates a femoral head of a human femur. It is to be understood, however, that the head portion could be formed in any shape which would adequately fill the patient's acetabular cavity to maintain the joint spacing of the implant area.

In a preferred arrangement, the pre-formed temporary hip prosthesis 10 will include a collar 26 formed at the juncture of the neck portion 14 and the elongated stem portion 12. When provided, the collar 26 is substantially disk-shaped and forms an acute angle with respect to the elongated stem portion 12 as depicted in FIG. 1. The pre-formed temporary hip prosthesis 10 normally further is cannulated, i.ee., provided with an elongated canal 28 which is adapted to accept an elongated removal tool 32, described in more detail below, to facilitate removal of the temporary hip prosthesis from the body. The elongated canal 28 extends from the upper proximal end 20 to the lower distal end 18 of the elongated stem portion 12. As illustrated in FIG. 2, the elongated canal 28 may be a substantially cylindrical aperture formed concentrically with the elongated stem portion 12.

As is illustrated in FIG. 3, the pre-formed temporary hip prosthesis 10 can be provided with a threaded aperture 30 in the upper portion 20 of the elongated stem portion 12 in exception or in addition to the elongated canal 28. The threaded aperture 30 is sized and configured to accept a threaded removal tool 38, discussed in more detail below, which may be used to facilitate removal of the pre-formed temporary hip prosthesis.

Each of the elongated stem portion 12, neck portion 14, and head portion 16 typically is composed of a bone cement such as polymethylmethacrylate ("PMMA"), commonly referred to as methylmethacrylate. These portions can be formed together in a single mold to form a one-piece temporary hip prosthesis, or separately with each portion being connected together at a later time. Accordingly, the pre-formed temporary hip prosthesis 10 can be unitary or modular in construction. In either case, bone cement is presently preferred because it is approved by the FDA for implantation into the human body.

Regardless of the particular material chosen for fabrication of the pre-formed temporary hip prosthesis 10, the material contains an antibiotic agent. It is currently anticipated that the antibiotic agent will impregnated into the material by simply mixing in an appropriate amount of antibiotic with the constituent elements of the material during the formation process of the temporary hip prosthesis 10. However, it will be understood that other methods of impregnation may be used, for example, soaking a porous, temporary hip prosthesis in a liquid antibiotic.

When it is determined that a joint replacement patient has contracted an infection, the physician must first determine if the primary prosthesis should be removed. If such removal is warranted, a surgeon will remove the entire prosthesis. In the case of a total hip replacement patient, removal will include the extraction of both the hip stem fixed within the canal of the femur and the acetabular cup fixed to the patient's pelvis. Once these components of the primary prosthesis have been removed, the surgeon will inspect the implant area to check for signs of infection and will determine the size and extent of the joint spacing of the patient. The magnitude of this spacing will vary with the size of the patient and with the size of the primary prosthesis which had previously occupied the implant area. After the size of the joint spacing has been ascertained, the physician may then select the correctly sized pre-formed temporary hip prosthesis for the particular patient. Typically, the physician will be provided with a variety of differently sized prostheses to more closely match the temporary hip prosthesis with the patient. In particular, the physician will have available several different sizes of stem portion diameters with which to choose from. Moreover, the physician will also be able to choose a preformed temporary hip prosthesis having a desired concentration of antibiotic impregnated therein. To simplify the selection process, it is preferred that each preformed temporary hip prosthesis is prepackaged in a sterile packet or container having indicia or other coding indicating the size of the prosthesis contained therein and its antibiotic concentration.

Once the selected pre-formed temporary hip prosthesis has been removed from its packaging, the prosthesis may be altered by the surgeon or surgical assistant to more closely correlate to the anatomy of the patient. Typically, the elongated stem portion 12 is approximately 200 to 250 mm long and the head portion has a radius of approximately 44 to 48 mm in length. Since the elongated stem portion 12 is substantially longer than the typical primary prosthesis stem, the elongated stem portion most often must be trimmed so that the length of the stem portion measured from the collar approximates the depth of the femoral canal of the patient. Trimming may be accomplished by cutting the elongated stem portion 12 with a common surgical tool such as a bone saw. Due to the heat formed during the cutting process, the opening of the elongated canal of the elongated stem portion typically needs to be reformed to remove any bone cement that has fused the opening shut. In that the head portion 16 of the temporary prosthesis is substantially larger than the typical femoral head of a primary prosthesis, it also may need to be reduced in size. However, since both the hip stem and the acetabular cup of the primary hip prosthesis will have been removed, it is anticipated that a large head portion will be needed in most applications to ensure that the full joint spacing is maintained. In fact, the surgeon may even need to increase the size of the head portion by adding on additional antibiotic-impregnated bone cement.

After the temporary hip prosthesis 10 has been trimmed and/or reshaped to the proper extent, the temporary hip prosthesis is inserted into the implant area. Specifically, the elongated stem portion 12 is inserted into the canal of the femur with the head portion 16 placed in the acetabular cavity of the hip. Overinsertion into the femoral canal is prevented with the collar 26, this collar abutting the top surface of the femur when the temporary hip prosthesis is fully inserted. The collar 26 furthermore prevents the temporary hip prosthesis 10 from creeping down into the canal during the recuperation period against the contractive force of the patient's tightening muscles and tendons.

Once the insertion procedure has been completed, the joint is immobilized and the patient being either bedridden or, at minimum, prohibited from putting weight on the joint in which the temporary hip prosthesis is provided. It is important that the patient be prevented from placing weight on the joint in that the temporary hip prosthesis is typically formed exclusively from bone cement which is far more brittle than the metals conventionally used in primary hip prostheses. However, it is to be noted that the temporary hip prosthesis is strong enough to withstand the contraction of the surrounding muscles and tendons of the patient during the recuperation period. During this time, the temporary hip prosthesis will be left in place, with the antibiotic agent impregnated into the bone cement leaching out to the surrounding tissue, preventing the formation of the infection in the implant area or destroying the infection if it had already formed.

Once the physician is satisfied that the infection has been overcome, the preformed temporary hip prosthesis 10 may be removed. Although the temporary hip prosthesis is not fixed in place in the manner in which primary prostheses are, tissue growth in the femoral canal may create difficulty in removing the temporary hip prosthesis. In cases in which the temporary hip prosthesis is provided with an elongated canal 28, an elongated removal tool 32 such as that depicted in FIG. 9 may be used to aid in the removal process. As shown in the figure, the removal tool can, for instance, be in the form of an elongated shaft 33 having a handle 34 and split ends provided with hooks 36 which, when inserted into the canal, are biased to spring out at the lower distal end 18 of the elongated stem portion 12 when the elongated removal tool is passed therethrough to firmly engage the temporary hip prosthesis. Once secured in this manner, the surgeon can remove the prosthesis simply by pulling it out with the handle 34. Alternatively, in cases in which the temporary hip prosthesis 10 is provided with a threaded aperture 30 at the upper proximal end 20 of the elongated stem portion 12, the temporary hip prosthesis may be removed with the aid of the threaded removal tool 38 depicted in FIG. 10. As illustrated in the figure, the threaded tool 38 can, for instance, take the form of a threaded bolt 40 provided with a handle 42. To remove the temporary hip prosthesis 10, the threaded tool 38 is inserted into the threaded aperture 30 and then the temporary hip prosthesis is pulled out from the femur by pulling outwardly on the handle 38. After the pre-formed temporary hip prosthesis has been removed, the femoral canal is then carefully cleaned with a lavage to ensure that no bone cement remains in the femur. At this point, a primary, weight bearing hip prosthesis may again be implanted in the patient's hip.

Although the above described pre-formed temporary hip prosthesis would function well to fight infection and maintain joint spacing in the implant area, approval has not yet issued from the FDA for the commercial manufacture of products formed solely of antibiotic-impregnated bone cement. Accordingly, until such approval is obtained, an interim solution to the problem is needed. The second embodiment of the invention provides such a solution. In this embodiment of the invention, the physician is provided with a prosthesis frame 44 such as that depicted in FIGS. 4–6. As illustrated in these figures, the hip prosthesis frame 44, similar to the pre-formed temporary hip prosthesis 10, comprises an elongated stem portion 46, a neck portion 48, and a head portion 50. Furthermore, the elongated stem portion 46 has a lower distal end 52 and an upper proximal end 54. Similarly, the neck portion 48 also has a lower distal end 56 and an upper proximal end 58, the neck portion 48 extending upwardly from the upper proximal end 54 of the elongated stem portion 46 at an angle to simulate the shape and configuration of a human femur. As shown in FIG. 5, the head portion 50 is connected to the upper proximal end 58 of the neck portion 48. In addition, the prosthesis frame 44 is provided with a collar 60 positioned at the juncture of the neck portion 48 and the elongated stem portion 46. Included on the collar 60 is an upper surface 62 which faces the head portion 50. Like the pre-formed temporary hip prosthesis, the prosthesis frame will typically be formed from bone cement.

Unlike the pre-formed temporary hip prosthesis 10, however, the elongated stem portion 46 of the prosthesis frame 44 is provided with a plurality of radial flanges 64 which extend from a central axis of the elongated stem portion. Although the elongated stem portion 46 is shown in FIGS. 4–7 as having four radial flanges 64, it is to be understood that a lesser or greater of radial flanges could be provided, as desired. As shown in these figures, the radial flanges 64 extend substantially along the entire length of the elongated stem portion 46. Configured in this manner, the radial flanges 64 provide a plurality of elongated recesses 66 which extend from the central axis of the elongated stem portion 46 to the outer edges 68 of each radial flange 64. These elongated recesses 66 are adapted to receive and support a hardenable material, such as bone cement, which is impregnated with an antibiotic. Thus, the frame 44 functions as the endoskeleton for the end product, and the stem portion 46 functions as a stem support for the stem of the final product.

Figure 4:
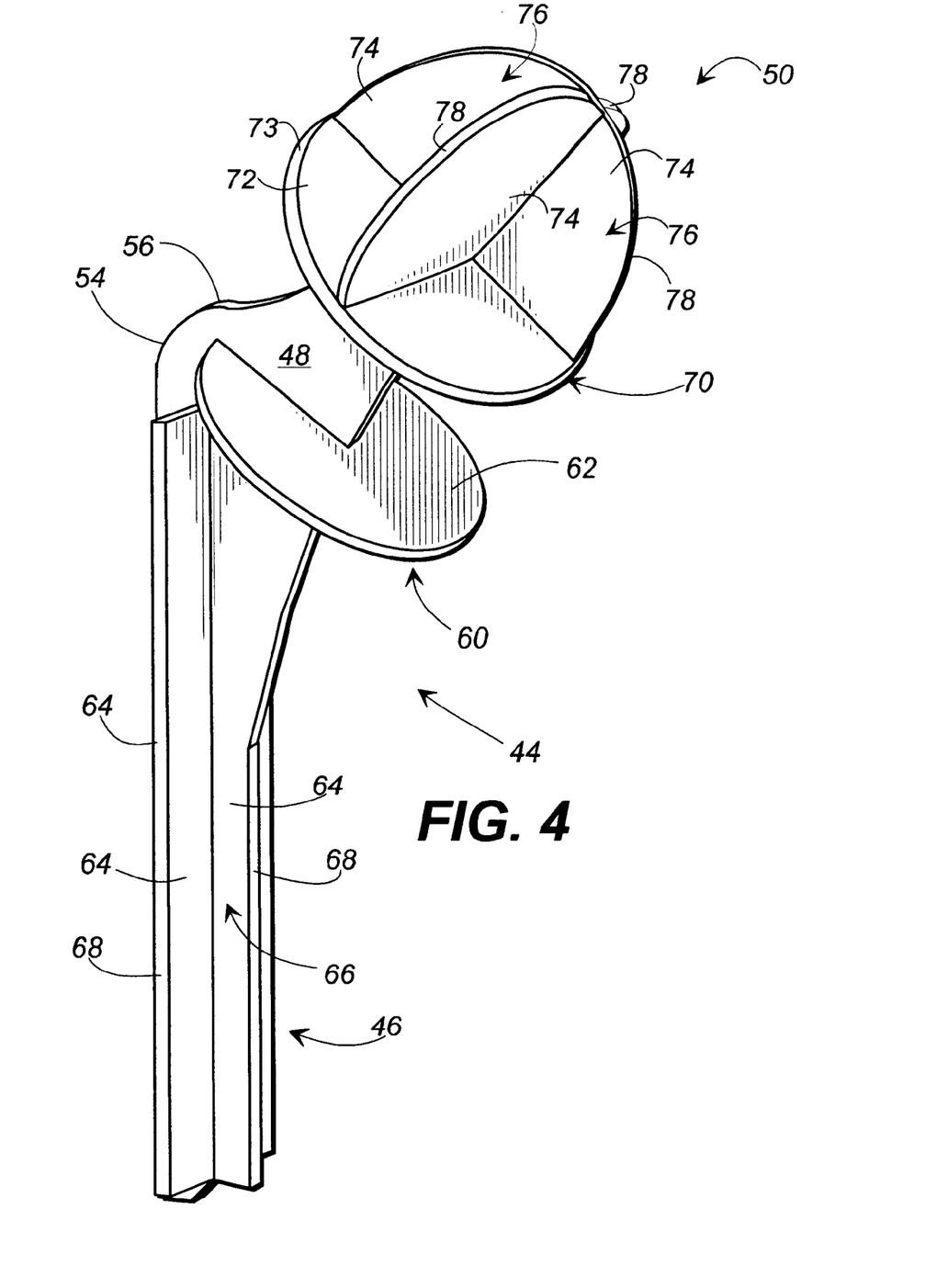
FIG. 4 is a perspective view of a prosthesis frame.
Figures 5, 6, 7:
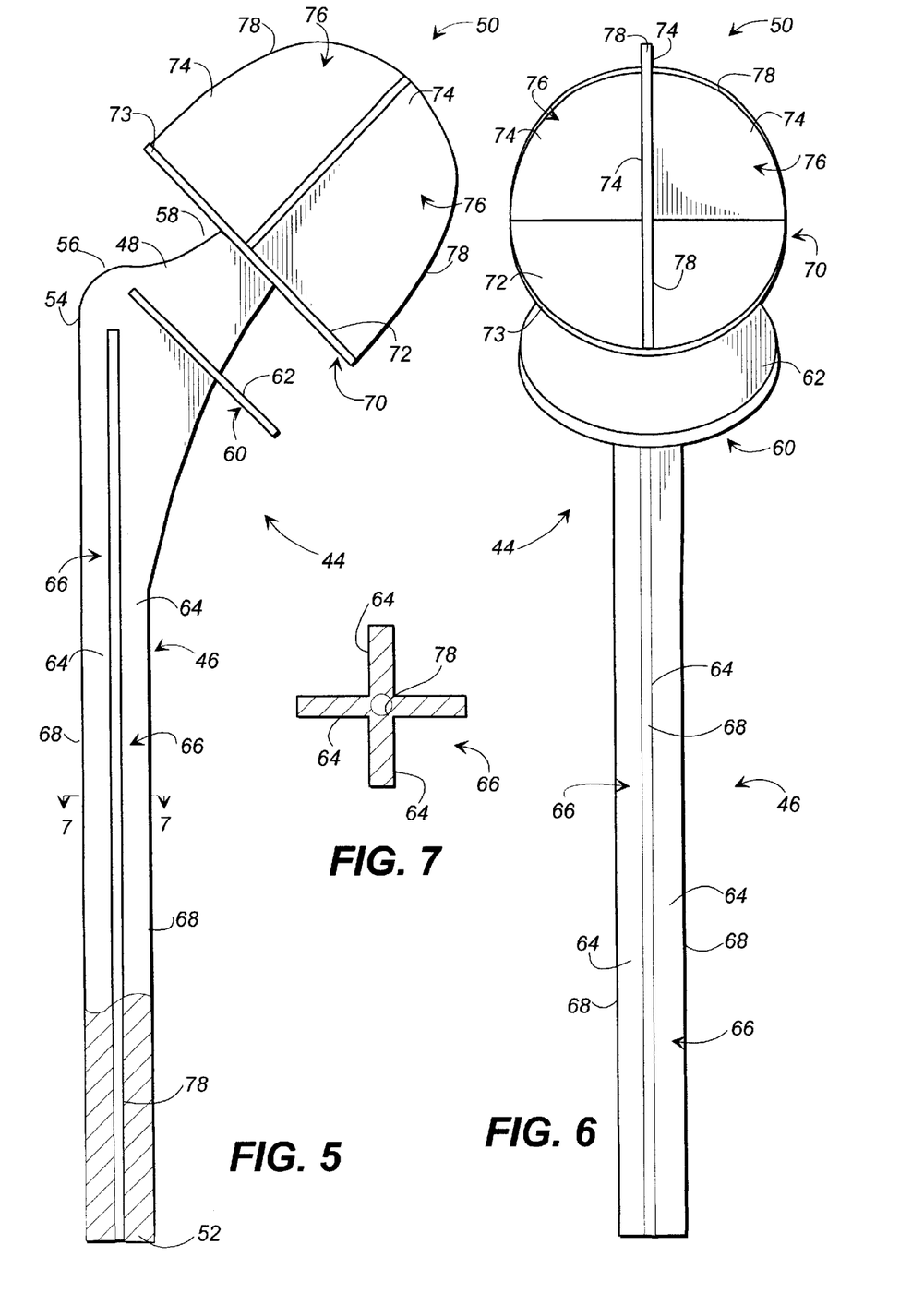
FIG. 5 is a side view of the prosthesis frame shown in FIG. 4.
FIG. 6 is a front view of the prosthesis frame shown in FIGS. 4–5.
FIG. 7 is a cross-sectional view of a stem portion of the prosthesis frame shown in FIGS. 4–6.

As illustrated in FIGS. 4–6, the head portion 50 comprises a substantially circular base portion 70 having a top surface 72 and an outer edge 73. Positioned atop the top surface 72 is a plurality of arcuate flange members 74 which extend upwardly from the top surface 72 and preferably meet along a central axis normal to the circular base portion 70. It is to be noted that although the head portion 50 is shown as having four flanges members 74, like the flanges 64 of the stem portion 46, a lesser or greater number of flange members could be used, as desired. Similar to the radial flanges 64, the arcuate flange members 74 provide a plurality of recesses 76 which extend outwardly toward the outer edges of the circular base portion 70 and each arcuate flange member 74. These recesses 76 also are adapted to receive and support a hardenable material, such as bone cement, which is impregnated with an antibiotic. Therefore, the head portion 50 functions as a ball support, for supporting the final ball that is formed on the prosthesis frame.

The prosthesis frame 44 may also be provided with means for facilitating its removal from the femoral cavity once the infection has been overcome. As illustrated in FIGS. 5 and 7, the elongated stem portion 46 of the prosthesis frame 44 typically is provided with an elongated canal 78 which extends from the upper proximal end 54 to the lower distal end 52 of the elongated stem portion 46. Although it is preferable to provide the prosthesis stem portion 46 with such a canal 78, the prosthesis frame 44 could alternatively be provided with a threaded metal sleeve (not shown) placed in the upper proximal end 54 of the elongated stem portion to provide a threaded aperture similar to threaded aperture 30 of the pre-formed temporary hip prosthesis 10 described above.

Figures 8, 9, 10:
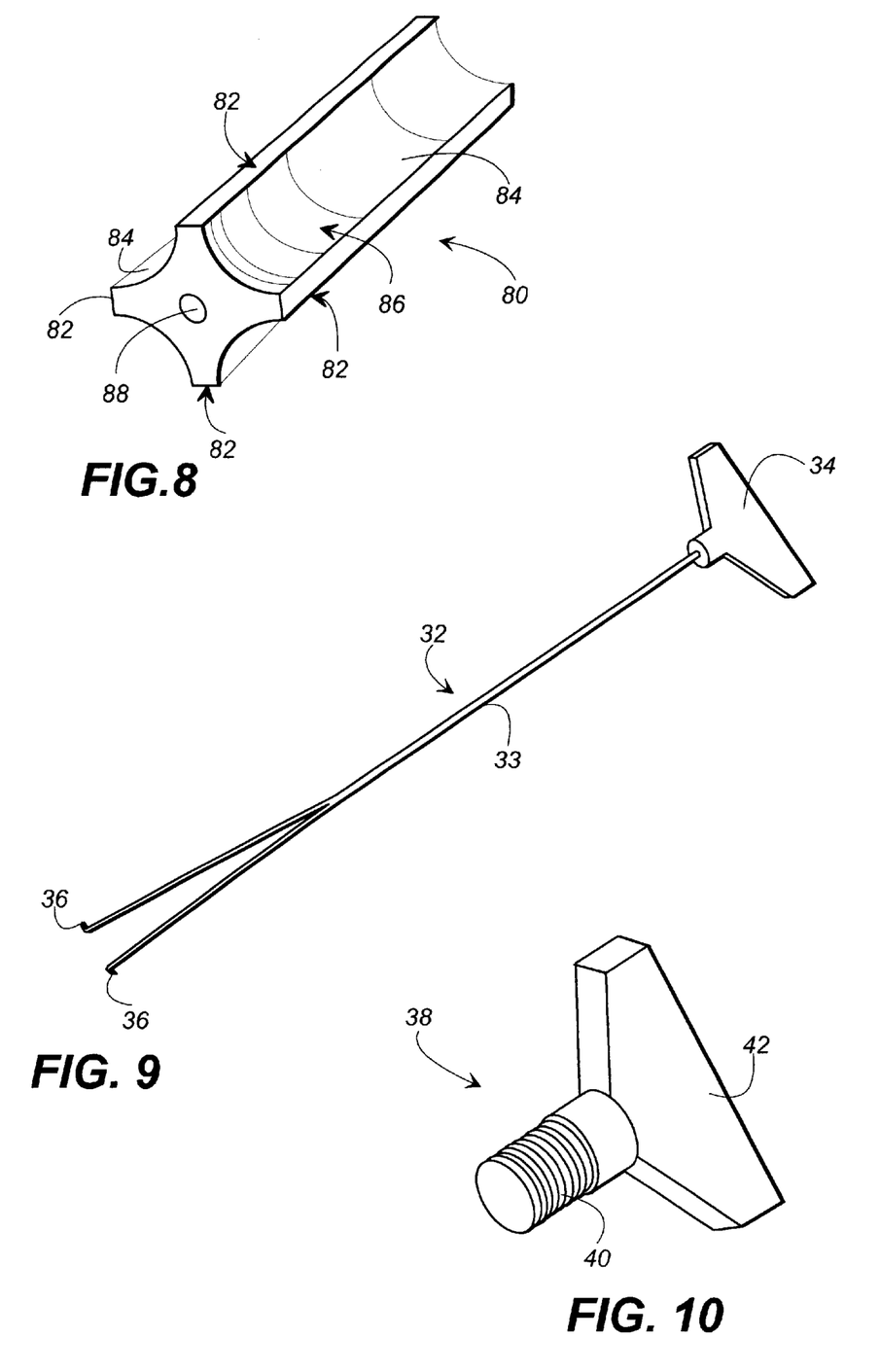
FIG. 8 is a perspective view of an alternative configuration of the stem portion of the prosthesis frame.
FIG. 9 is a perspective view of an elongated removal tool.
FIG. 10 is a perspective view of threaded removal tool.

FIG. 8 depicts an alternative arrangement of the elongated stem portion 46 of the prosthesis frame 44. In this embodiment, the elongated stem portion 80 is provided with curved radial flanges 82 formed from concave channels 84 extending along the length of the elongated stem portion 80 such that the elongated stem portion has a substantially star-shaped cross-section. Each of the concave channels 84 provide elongated recesses 86 which, similar to the above described recesses, may be filled with antibiotic-impregnated bone cement. As with the first configuration of the elongated stem portion 46 of the prosthesis frame, the alternative elongated stem portion 80 also can be provided with an elongated canal 88 or a threaded sleeve (not shown) to facilitate removal of the temporary prosthesis after the infection has been overcome. Although not depicted in the figures, the arcuate flange members 74 of the head portion 50 likewise can be formed from concave surfaces, if desired. When the frame is formed with curved radial flanges and curved arcuate flange members as described above, less antibiotic-impregnated hardenable material and less time will be required to form the temporary prosthesis.

The prosthesis frame is used in a manner similar to that of the pre-formed temporary hip prosthesis. When it is determined that a joint implant must be removed due to infection, the physician removes the entire prosthesis and inspects the implant area to determine the size and extent of the joint spacing of the patient. After the size of the joint spacing has been ascertained, the physician then selects a prosthesis frame appropriate for the particular application. It is anticipated that only one size prosthesis frame will be required for each application whether it be a hip stem prosthesis frame, knee prosthesis frame, or otherwise. It will be understood, however, that a variety of differently sized prostheses could be made available to the physician to more closely match the particular patient. Like the pre-formed temporary hip prosthesis described above, each prosthesis frame is prepackaged in a sterile packet or container having indicia or other coding that indicates the size and antibiotic concentration of the prosthesis contained therein.

Once the appropriate prosthesis frame 44 has been selected, it can be altered by the surgeon or surgical assistant to more closely correlate to the particular patient. In the case of a hip prosthesis frame described above, the elongated stem portion is normally approximately 200 to 250 mm long, and the outer edges of the circular base portion 70 and the arcuate flanges 74 will form the outline of a semi-sphere having a radius approximately 44 to 48 mm in length. Most often, the elongated stem portion will need to be trimmed so that its length approximates the depth of the femoral canal of the patient. Where the prosthesis frame is provided with an elongated canal, the opening of the canal may need to be reformed due to fusion of the opening resulting from heat formed during the cutting process.

Figure 11:
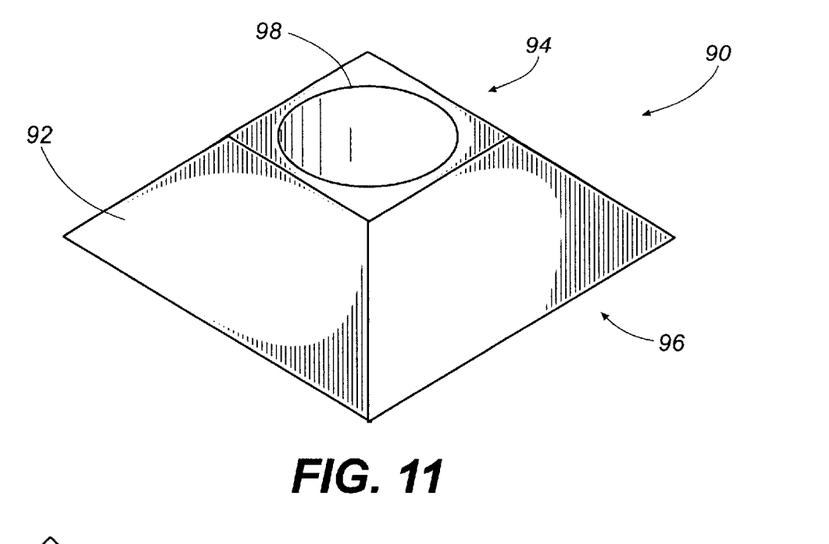
FIG. 11 is a perspective view of a mold used with the prosthesis frame shown in FIGS. 4–7.
Figure 12:
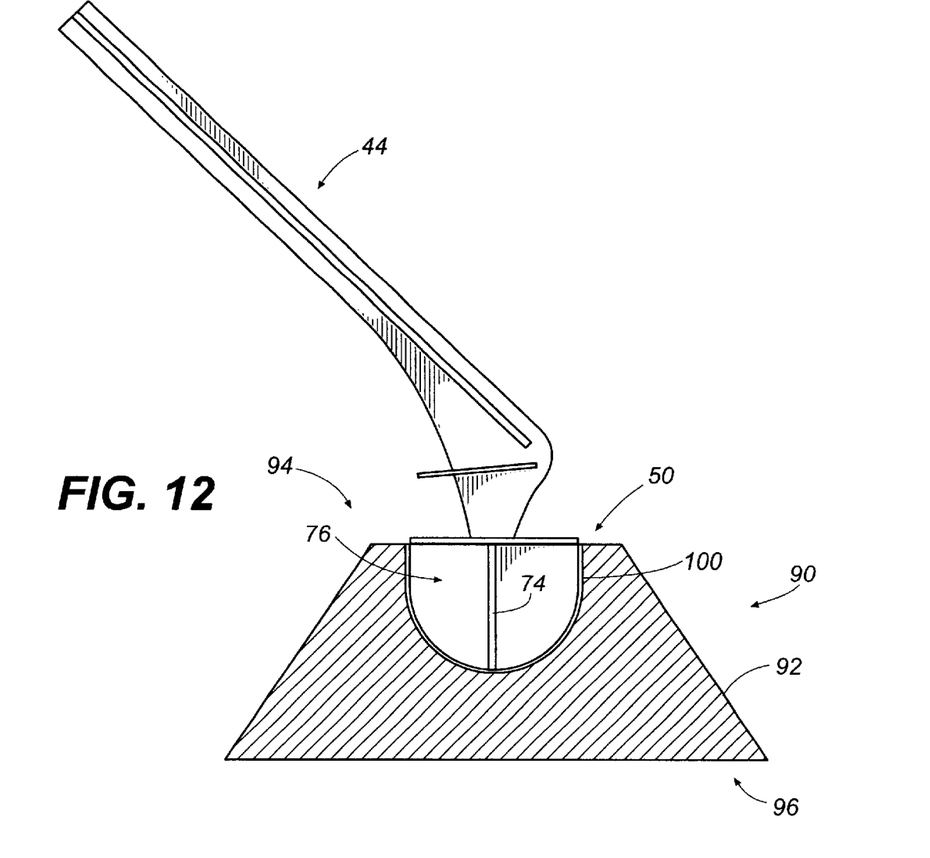
FIG. 12 shows the prosthesis frame of FIGS. 4–7 in use with the mold of FIG. 11.

After the temporary hip prosthesis frame 44 has been trimmed, an antibiotic-impregnated hardenable material can be manually applied to the recesses 66 and 76 of the prosthesis frame. The hardenable material, preferably PMMA bone cement, is liberally applied in the recesses 66 and 76 until it is substantially flush with the outer edges of the radial flanges, the circular base portion, and the arcuate flange members thereby forming a temporary hip prosthesis having a substantially cylindrical shank and a substantially bulbous head. In addition, the neck portion of the frame between the collar and the base portion may also be provided with antibiotic-impregnated bone cement, if desired. To simplify the process of applying the antibiotic-impregnated hardenable material to the hip prosthesis frame 44, a mold 90 can be used by the surgeon or surgical assistant. As shown in FIG. 11, this mold can comprise a body portion 92 having a top 94 and a base to 96. Formed in the top 94 of the body portion 92, is an opening 98 that leads to an inner cavity 100 (FIG. 12). As is illustrated in the cross-sectional view of FIG. 12, this inner cavity 100 is sized and configured so as to receive the head portion 50 of the prosthesis frame 44 with little clearance. With this arrangement, the entire head portion 50 of the prosthesis frame can be disposed within the inner cavity 100 to apply to the hardenable material to the recesses 76 formed therein. To accomplish this application, the inner cavity 100 of the mold 90 is filled with uncured hardenable material and the head portion 50 of the prosthesis frame 44 dipped into the cavity such that the recesses 76 are filled with the uncured hardenable material. The prosthesis frame 44 then can be left in this position relative to the mold 90 until the hardenable material fully cures. At this point, the prosthesis frame 44 can be removed from the mold 90 with the hardeanble material filling the recesses 76 such that the head portion is configured as a substantially bulbous head that is substantially flush with the outer edges of the arcuate flanges 74.

Once the hardenable material has adequately cured, the newly formed temporary hip prosthesis, or other non-weight bearing temporary prosthesis, is inserted into the implant area. Next, the limb will be immobilized to prevent the patient from putting weight on the joint. As with the preformed temporary hip prosthesis 10, the temporary prosthesis formed from the prosthesis frame 44 will be left in place for several weeks during which time the antibiotic will leach out to the surrounding tissue to destroy the infection. Once the infection has been eradicated, the temporary prosthesis may be removed. In cases where the temporary prosthesis is a hip prosthesis provided with an elongated canal 78 or 88, an elongated removal tool 32 similar to that depicted in FIG. 9 may be used to aid in the removal process. Alternatively, in cases in which the temporary hip prosthesis is provided with a threaded sleeve at the upper proximal end 54 of the elongated stem portion, the temporary hip prosthesis may be removed with the aid of the threaded removal tool 38 depicted in FIG. 10.

In an alternative method of fighting infection and maintaining joint spacing in an implant area, a temporary prosthesis is formed by the surgeon with the use of a prosthesis mold. After the size of the joint spacing has been ascertained, the surgeon or a surgical assistant selects a prosthesis mold which is configured to produce a temporary prosthesis of a size appropriate for the particular infected patient. It is anticipated that a variety of differently sized prosthesis molds could be made available to the surgical staff to closely match the patient's anatomy. Once the appropriate prosthesis mold has been selected, the surgeon or surgical assistant mixes the hardenable material with a predetermined amount of antibiotic and fills the mold such that the entire inner space of the mold is occupied with antibiotic-impregnated hardenable material. Once the material has adequately hardened, the newly formed temporary prosthesis can be removed and shaped, if necessary, to accommodate the implant patient. At this point, the temporary prosthesis is inserted into the implant area in accordance with the above described methods.

While the forgoing invention has been described in the form of preferred embodiments and procedures, it will be understood by those skilled in the art that numerous modifications, variations, and changes, can be made thereto without departure from the spirit and scope of the invention as set forth in the following claims.

I claim:

1. A prosthesis frame for forming a temporary hip prosthesis to be placed in an implant area of the human body, said prosthesis frame comprising:

an elongated stem portion having a lower distal end and an upper proximal end, said elongated stem portion further including radial flanges extending along the length of said stem portion;

a neck portion having a lower distal end and an upper proximal end, the lower distal end of said neck portion being connected to said upper proximal end of said elongated stem portion, said neck portion extending upwardly from said elongated stem portion; and a head portion connected to said upper proximal end of said neck portion, said head portion including a substantially circular base portion having a top surface and further including at least one arcuate flange member extending from said top surface;

wherein said radial flanges of said elongated stem portion and said at least one arcuate flange member form recesses that can be filled with antibiotic-impregnated hardenable material to form a temporary hip prosthesis which can be inserted into the implant area in place of a primary prosthesis with the antibiotic leaching out of said hardenable material to fight infection and said head portion maintaining adequate joint spacing in opposition to contraction of the muscles and tendons of the patient so that a primary hip prosthesis can be implanted into the implant area after the infection has been overcome.

2. The prosthesis frame of claim 1, wherein said frame is composed of polymethylmethacrylate.

3. The prosthesis frame of claim 2, wherein said neck portion is provided with a collar which will abut a top surface of the femur during insertion of said temporary hip prosthesis into the implant area to limit insertion of said elongated stem portion into the femoral canal of the patient.

4. The prosthesis frame of claim 2, wherein said head portion includes a plurality of arcuate flange members each having an outer edge, said outer edges of said arcuate flange members together substantially forming the outline of a semisphere so that a substantially bulbous head can be formed by filling said recesses until said antibiotic-impregnated hardenable material is substantially flush with said outer edges of said arcuate flange members.

5. The prosthesis frame of claim 2, wherein said elongated stem portion includes a plurality of radial flanges each having an outer edge, said outer edges of said radial flanges together substantially forming the outline of an elongated cylinder so that a substantially cylindrical shank can be formed by filling said recesses formed by said radial flanges until said antibiotic-impregnated hardenable material is substantially flush with said outer edges of said radial flanges.

6. The prosthesis frame of claim 2, wherein said recesses formed by said radial flanges of said elongated stem portion are formed in the shape of elongated concave channels such that said prosthesis frame has a substantially star-shaped cross-section.

7. The prosthesis frame of claim 2, wherein said elongated stem portion is provided with an elongated canal extending from said upper proximal end of said elongated stem portion to said lower distal end of said elongated stem portion to permit the passage of an elongated removal tool used to remove said temporary hip prosthesis from the implant area.

8. The prosthesis frame of claim 2, wherein said upper proximal end of said elongated stem portion is provided with a threaded aperture which is adapted to accept a threaded removal tool used to remove said temporary hip prosthesis.

9. The prosthesis frame of claim 2, wherein said at least one arcuate flange of said head portion has a radial dimension approximately between 44 and 48 mm.

10. The prosthesis frame of claim 2, wherein said elongated stem portion is approximately between 200 and 250 mm in length.

* * * * *